United States Patent
Ruan

(10) Patent No.: US 11,541,095 B2
(45) Date of Patent: Jan. 3, 2023

(54) NASAL BALM FOR RELIEVING ALLERGIC RHINITIS SYMPTOMS

(71) Applicant: Shenzhen YuanguangzhouTechnology Co., Ltd., Shenzhen (CN)

(72) Inventor: Jing Ruan, Shenzhen (CN)

(73) Assignee: SHENZHEN YUANGUANGZHOU TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/839,099

(22) Filed: Apr. 3, 2020

(65) Prior Publication Data

US 2020/0316156 A1 Oct. 8, 2020

Related U.S. Application Data

(63) Continuation-in-part of application No. PCT/CN2019/096932, filed on Jul. 20, 2019.

(30) Foreign Application Priority Data

Apr. 3, 2019 (CN) .......................... 201910264355.4

(51) Int. Cl.
| | | |
|---|---|---|
| *A61K 36/752* | (2006.01) | |
| *A61K 9/00* | (2006.01) | |
| *A61K 36/185* | (2006.01) | |
| *A61K 36/22* | (2006.01) | |
| *A61K 47/44* | (2017.01) | |

(52) U.S. Cl.
CPC .......... *A61K 36/752* (2013.01); *A61K 9/0043* (2013.01); *A61K 36/185* (2013.01); *A61K 36/22* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 9,468,595 B2 * | 10/2016 | Carlson | ............... | C08F 222/385 |
| 2020/0375877 A1 * | 12/2020 | Mackin | .................... | A61K 8/39 |

FOREIGN PATENT DOCUMENTS

| | | |
|---|---|---|
| AU | 2014101455 A4 | 1/2015 |
| CN | 103494739 A | 1/2014 |
| CN | 105535196 A | 5/2016 |
| CN | 107126462 A | 9/2017 |
| CN | 107582783 A | 1/2018 |
| CN | 109528576 A | 3/2019 |
| WO | WO 2012/035065 * | 3/2012 |

OTHER PUBLICATIONS

Byrdie, Marula oil for skin, 26 pages, 2021.*
Yuan Yao et al., Advances in the Treatment of Rhinitis and the Development of Aromatherapy, Asia-Pacific Traditional Medicine, Nov. 2017, pp. 50-53, vol. 13, No. 21, Hubei Provincial Science and Technology Communication Co., Ltd., China.

* cited by examiner

*Primary Examiner* — Michael V Meller
(74) *Attorney, Agent, or Firm* — Nixon & Vanderhye P.C.

(57) ABSTRACT

A nasal balm including, by weight, 10-50% of shea butter; 10-50% of coconut oil; 10-50% of *Cera alba*; 1-5% of grapefruit peel oil; 1-10% of *Sclerocarya birrea* seed oil; 1-10% of *Moringa pterygosperma* seed oil; and 1-10% of *Simmondsia chinensis* seed oil.

7 Claims, 2 Drawing Sheets

NASAL BALM FOR RELIEVING ALLERGIC RHINITIS SYMPTOMS

CROSS-REFERENCE TO RELATED APPLICATIONS

This application is a continuation-in-part of International Patent Application No. PCT/CN2019/096932 with an international filing date of Jul. 20, 2019, designating the United States, and further claims priority benefits to Chinese Patent Application No. 201910264355.4 filed Apr. 3, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a nasal balm for relieving allergic rhinitis symptoms.

The treatment of pollen allergy mainly depends on steroids and antihistamines, but these drugs have side effects, such as drowsiness, depression and so on. Although the patients can wear masks to reduce allergens, long-term wearing masks adversely affects the respiration.

SUMMARY

The disclosure provides a nasal balm for relieving allergic rhinitis symptoms.

The nasal balm comprises, by weight, 10-50% of shea butter; 10-50% of coconut oil; 10-50% of *Cera alba;* 1-5% of grapefruit peel oil; 1-10% of *Sclerocarya birrea* seed oil; 1-10% of *Moringa pterygosperma* seed oil; and 1-10% of *Simmond siachinensis* seed oil.

The shea butter is cold pressed and unrefined solid.

The coconut oil, the grapefruit peel oil, the *Sclerocarya birrea* seed oil, the *Moringa pterygosperma* seed oil, and the *Simmondsia chinensis* seed oil are extracted by cold pressing method.

The nasal balm further has a fruit scent.

The disclosure also provides a method for preparing the nasal balm, the method comprising:

1) weighing, by weight, 10-50% of shea butter; 10-50% of coconut oil; 10-50% of *Cera alba;* 1-5% of grapefruit peel oil; 1-10% of *Sclerocarya birrea* seed oil; 1-10% of *Moringa pterygosperma* seed oil; 1-10% of *Simmondsia chinensis* seed oil; and 0-1% lavender;
2) heating and stirring the *Cera alba* in a water bath to 65-70° C., to yield a first component;
3) mixing the shea butter and the coconut oil, and heating and stirring a mixture of the shea butter and the coconut oil in a water bath to 60-70° C., to yield a second component;
4) mixing the grapefruit peel oil, the *Sclerocarya birrea* seed oil, the *Moringa pterygosperma* seed oil, and the *Simmondsia chinensis* seed oil, and heating and stirring a mixture of the grapefruit peel oil, the *Sclerocarya birrea* seed oil, the *Moringa pterygosperma* seed oil, and the *Simmondsia chinensis* seed oil in a water bath to 60-65° C., to yield a third component;
5) mixing the first component and the second component and stirring, to yield a mixed material; and
6) mixing the third component, the mixed material, and lavender, stirring, and cooling to room temperature.

The stirring of materials in 2)-6) is performed in a stainless-steel reactor.

DETAILED DESCRIPTION OF THE EMBODIMENTS

Figure 1:
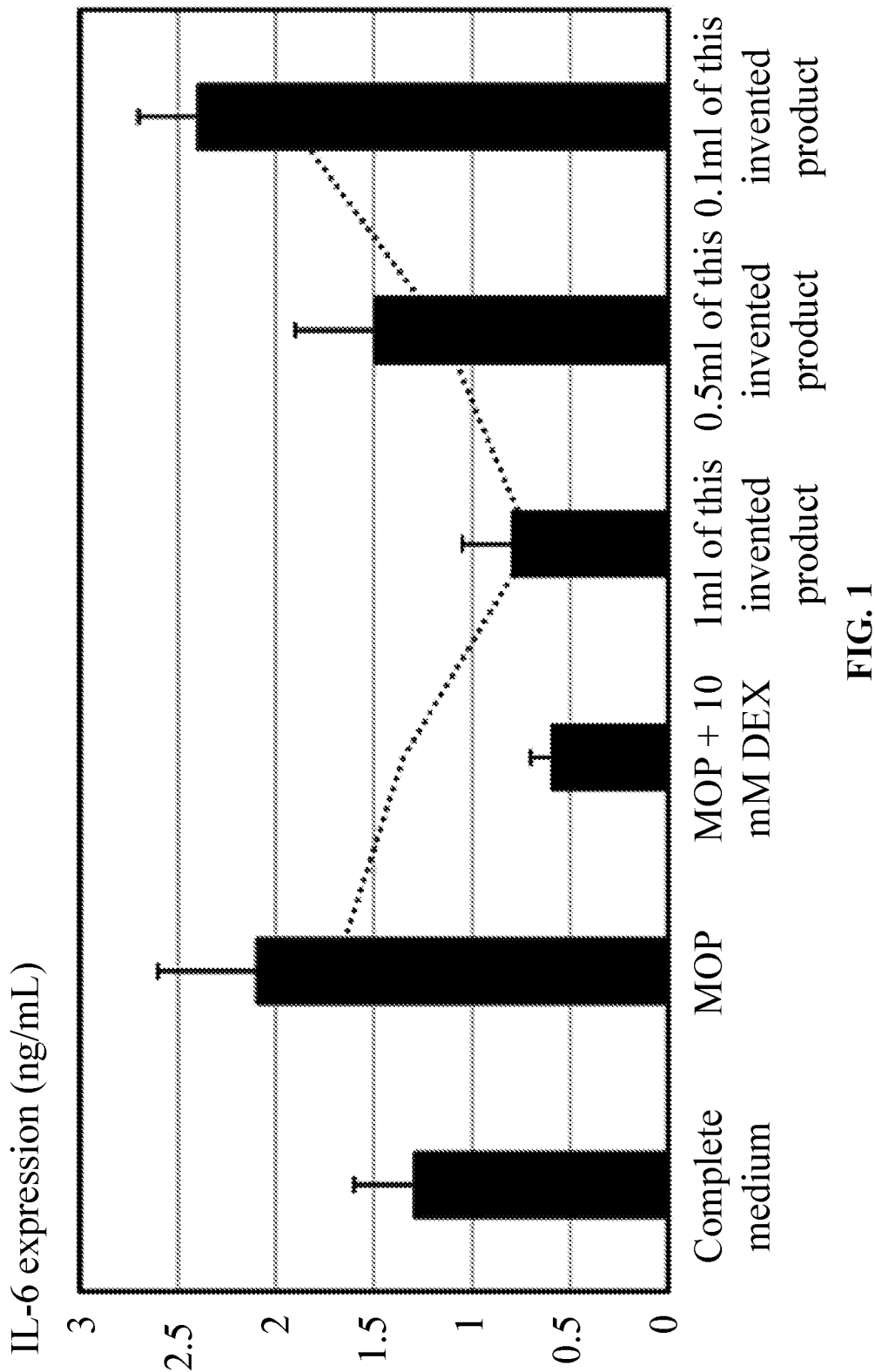
FIG. 1 shows the level of IL-6 in the epidermis treated with a mixture of pollutants and the nasal balm of the disclosure.
Figure 2:
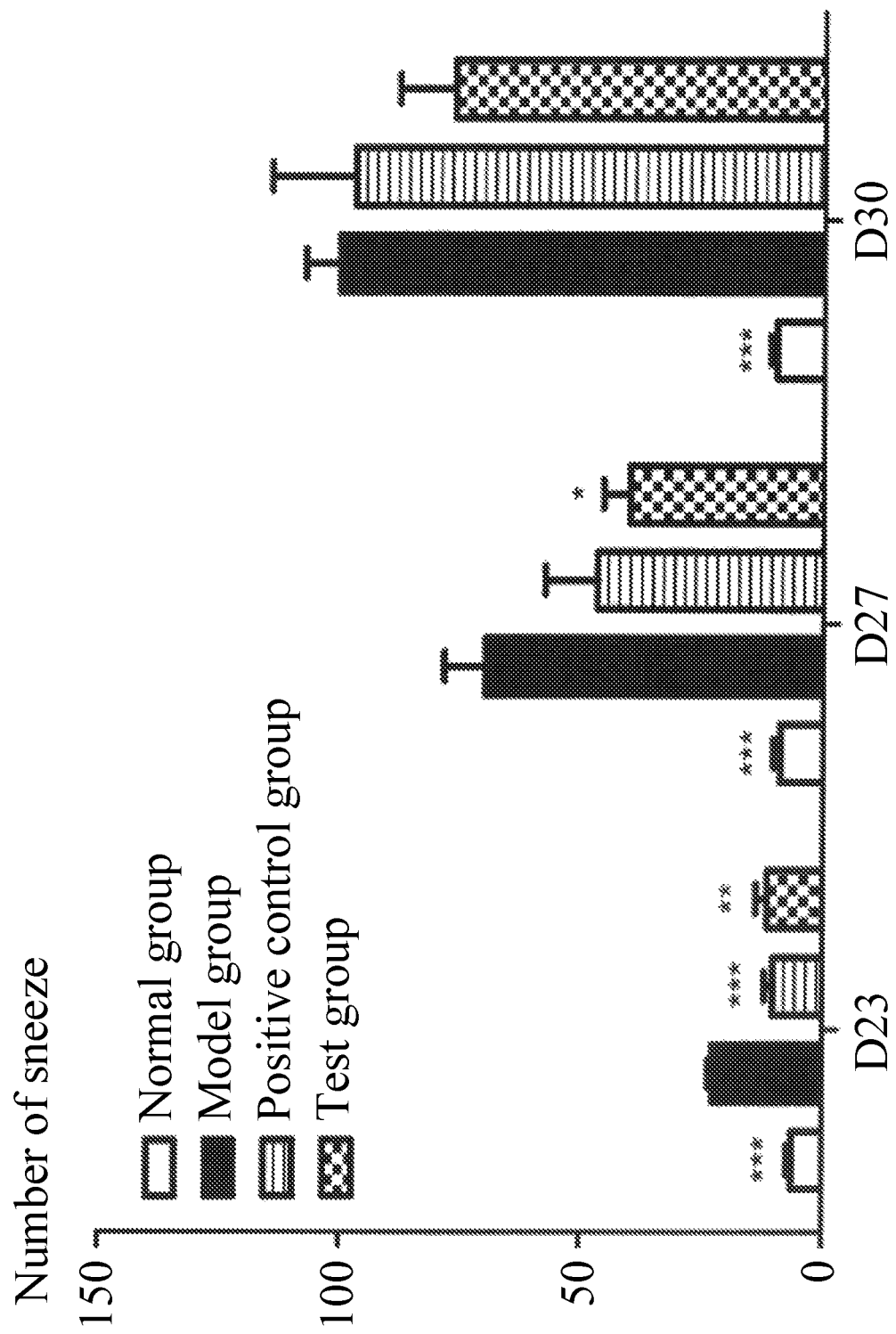
FIG. 2 shows a statistical graph of sneeze number of the mice in different groups according to one embodiment of the disclosure.

To further illustrate, embodiments detailing a nasal balm for relieving allergic rhinitis symptoms are described below. It should be noted that the following embodiments are intended to describe and not to limit the disclosure.

Example 1

A nasal balm for relieving allergic rhinitis symptoms comprises, by weight, 20% of shea butter; 40% of coconut oil; 20% of *Cera alba;* 1% of grapefruit peel oil; 10% of *Sclerocarya birrea* seed oil; 5% of *Moringa pterygosperma* seed oil; and 4% of *Simmondsia chinensis* seed oil.

The nasal balm is prepared as follows:
weighing the shea butter, the coconut oil, the *Cera alba*, the grapefruit peel oil, the *Sclerocarya birrea* seed oil, the *Moringa pterygosperma* seed oil, and the *Simmondsia chinensis* seed oil in proportion;
heating and stirring the *Cera alba* in a water bath to 65-70° C., to yield a first component;
mixing the shea butter and the coconut oil, and heating and stirring a mixture of the shea butter and the coconut oil in a water bath to 60-70° C., to yield a second component;
mixing the grapefruit peel oil, the *Sclerocarya birrea* seed oil, the *Moringa pterygosperma* seed oil, and the *Simmondsia chinensis* seed oil, and heating and stirring a mixture of the grapefruit peel oil, the *Sclerocarya birrea* seed oil, the *Moringa pterygosperma* seed oil, and the *Simmondsia chinensis* seed oil in a water bath to 60-65° C., to yield a third component;
mixing the first component and the second component and stirring, to yield a mixed material; and
mixing the third component and the mixed material, stirring, and cooling to room temperature.

The stirring of materials in 2)-6) is performed in a stainless-steel reactor.

Example 2

A nasal balm for relieving allergic rhinitis symptoms comprises, by weight, 10% of shea butter; 50% of coconut oil; 30% of *Cera alba;* 4% of grapefruit peel oil; 2% of *Sclerocarya birrea* seed oil; 3% of *Moringa pterygosperma* seed oil; and 1% of *Simmondsia chinensis* seed oil.

The nasal balm is prepared following the operations in Example 1.

Example 3

A nasal balm for relieving allergic rhinitis symptoms comprises, by weight, 50% of shea butter; 10% of coconut oil; 10% of *Cera alba*; 4% of grapefruit peel oil; 6% of *Sclerocarya birrea* seed oil; 10% of *Moringa pterygosperma* seed oil; and 10% of *Simmondsia chinensis* seed oil.

The nasal balm is prepared following the operations in Example 1.

Example 4

A nasal balm for relieving allergic rhinitis symptoms comprises, by weight, 15% of shea butter; 25% of coconut oil; 50% of *Cera alba*; 3% of grapefruit peel oil; 1% of *Sclerocarya birrea* seed oil; 1% of *Moringa pterygosperma* seed oil; and 5% of *Simmondsia chinensis* seed oil.

The nasal balm is prepared following the operations in Example 1.

Example 5

A nasal balm for relieving allergic rhinitis symptoms comprises, by weight, 20% of shea butter; 40% of coconut oil; 20% of *Cera alba*; 1% of grapefruit peel oil; 9% of *Sclerocarya birrea* seed oil; 5% of *Moringa pterygosperma* seed oil; 4% of *Simmondsia chinensis* seed oil and 1% of lavender.

The nasal balm is prepared as follows:
weighing the shea butter, the coconut oil, the *Cera alba*, the grapefruit peel oil, the *Sclerocarya birrea* seed oil, the *Moringa pterygosperma* seed oil, and the *Simmondsia chinensis* seed oil in proportion;
heating and stirring the *Cera alba* in a water bath to 65-70° C., to yield a first component;
mixing the shea butter and the coconut oil, and heating and stirring a mixture of the shea butter and the coconut oil in a water bath to 60-70° C., to yield a second component;
mixing the grapefruit peel oil, the *Sclerocarya birrea* seed oil, the *Moringa pterygosperma* seed oil, and the *Simmondsia chinensis* seed oil, and heating and stirring a mixture of the grapefruit peel oil, the *Sclerocarya birrea* seed oil, the *Moringa pterygosperma* seed oil, and the *Simmondsia chinensis* seed oil in a water bath to 60-65° C., to yield a third component;
mixing the first component and the second component and stirring, to yield a mixed material; and
mixing the third component, the mixed material, and lavender, stirring, and cooling to room temperature.

In Examples 1-5, the shea butter is cold pressed and unrefined solid.

The coconut oil, the grapefruit peel oil, the *Sclerocarya birrea* seed oil, the *Moringa pterygosperma* seed oil, and the *Simmondsia chinensis* seed oil are extracted by cold pressing method instead of heating or distillation.

Example 6

The nasal balm is light-yellow, has passed microbiological test (see Table 1) and hygienic chemical test (see Table 2), and meets the requirements of Safety and Technical Standards for Cosmetics (2015 Edition, China).

TABLE 1

Results of microbiological test of the nasal balm

| Item | Results | Limit value |
| --- | --- | --- |
| Total number of bacteria (CFU/g) | <10 | ≤1000 |
| Total number of molds and yeasts (CFU/g) | <10 | ≤100 |
| Thermotolerant coliforms/g | Not detected | / |
| *Staphylococcus aureus*/g | Not detected | / |
| *Pseudomonas aeruginosa*/g | Not detected | / |

TABLE 2

Results of hygienic chemical test of the nasal balm

| Item | Unit | Result | Method | Concentration | Limit value |
| --- | --- | --- | --- | --- | --- |
| Mercury (Hg) | mg/kg | <0.002 | The first method: Hydride atomic fluorescence spectrometry | 0.002 | ≤1 |
| Arsenic (As) | mg/kg | <0.01 | The first method: Hydride atomic fluorescence spectrometry | 0.01 | ≤2 |
| Lead (Pb) | mg/kg | <1.5 | The second method: Flame atomic absorption spectroscopy | 1.5 | ≤10 |
| Cadmium (Cd) | mg/kg | <0.18 | The second method Flame atomic absorption spectroscopy | 0.18 | ≤5 |

The product reduces the amount of allergen in the nose through the absorption and blocking effect, thereby blocking the pollen particles, and is particularly suitable for alleviating pollen allergy. After testing, it can not only significantly reduce the inflammation on the skin barrier, but also greatly relieve the symptoms in bad weather conditions.

1. The Effect of the Balm on Reducing the Symptoms of Pollen Allergy

In China, the United States, and Canada, volunteers aged between 10 to 65 years old with pollen or dust allergy symptoms were selected to use the product, and the effect of the product was investigated by questionnaire. Each volunteer used the product for five days. They answered the questionnaire and rated in three categories: sneezing, nasal congestion, and nasal discharge, whether the product helps to relieve the symptoms. The ratios of positive ratings against the entire samples are employed to measure the product's effectiveness. The allergic reactions of these volunteers to pollen are shown in Table 3.

TABLE 3

| Symptoms | Percent of people with alleviated symptoms |
| --- | --- |
| Sneeze | 78.72% |
| Nasal congestion | 74.47% |
| Nasal discharge | 68.09% |

2. Release of Pro Inflammatory Cytokine (1) Skin model: the effect of the balm of the disclosure was tested on a reconstructed epidermis. The normal human epidermal keratinocytes were cultured to form a three-dimensional, multi-layered, highly differentiated model of adult epidermis. The model exhibited normal barrier function (well differentiated cuticle). The skin model is provided by CellSystem (Troisdorf), used for the model of particulate matter (PM) and heavy metal pollution.

(2) Tissue preparation: the epidermis tissue was stored at 4° C. and cultured in 0.9 mL hydrocortisone medium (37° C.). Before use, the epidermis tissue was taken from the agarose shipping tray and placed in a six-hole plate. The tissue was incubated at 37° C. and 5% $CO_2$ for at least one hour. After this initial incubation, the medium was freshened (37° C.). Four tissue samples were prepared for each treatment.

(3) Main pollution model: atmospheric PM: a human skin model was reconstructed as an integrated three-dimensional cell culture model to simulate human skin in vitro. The model showed normal barrier function (with well differentiated cuticle).

(4) 0.1, 0.5 or 1 mL of the balm of the disclosure and 100 µL of a mixture of pollutants (MOP) were applied to the epidermis. The epidermis was washed daily with phosphate buffered saline (PBS) and was treated with the balm and MOP at 37° C. in the presence of 5% $CO_2$. In the presence of MOP, 10 µm of dexamethasone (DEX) was used as a control group. After 48 hours of incubation, 3-(4,5-dimethylthiazol-2-yl)-2,5-diphenyltetrazolium bromide (MTT) assay was used to determine the change of tissue viability. The epidermis was collected in a cell culture medium and stored at −70° C. until the level of IL-6 was evaluated. All experiments were repeated three times.

(5) IL-6 measurement: the concentration of the IL-6 was determined according to the manufacturer's instructions by using the commercial ELISA Kit (900-t16, Peprotech, USA).

(6) Results: as shown in the sole figure, the product of the disclosure has obvious inhibition on IL-6 release, and 1 mL of the product can reduce IL-6 by more than 62%. The decrease of IL-6 in the epidermis treated with MOP indicates the decrease of inflammation, which can improve and strengthen the protective barrier function of skin.

The raw materials of the nasal balm are nature and contain no hormone, so it is safe. The *Sclerocarya birrea* seed oil and the *Simmondsia chinensis* seed oil can prevent the dryness of the nasal cavity. The coconut oil and the grapefruit peel oil are natural preservatives, thus minimizing the risk of contamination of the balm.

Example 7

1. Experimental objective: to study the effect of the nasal balm of the disclosure on the allergic rhinitis of BALB/c mice.

2. Materials:

2.1 Test subject: the nasal balm of the disclosure 2.2 Positive control: Levocabastine hydrochloride nasal spray (Levocabastine), Janssen Pharmaceutical Ltd. Batch No: ILB2B00.

2.3 Normal control: Physiological saline solution, Qingzhou Yao Wang Pharmaceutical Co., Ltd. Batch No: 3219042803.

2.4 Other agents

Ovalbumin, Sigma, Batch No.: SLBQ9036V

Aluminum hydroxide gel, Thermo, Batch No.: SJ255649

2.5 The formulation of ovalbumin (OVA) solution 2 mg of OVA powder was weighed, dissolved with physiologic saline solution. The final volume was calibrated accurately to 14 mL. 3.5 mL of the OVA solution was pipetted into a 5 mL Eppendorf tube, followed by the addition of 0.5 mL of uniform aluminum hydroxide gel, and then the OVA solution was dropwise added. The mixture was shaken for 30 min, and then 0.2 mL of the resulting solution was injected to each mouse to induce the sensitization.

2.6 Preparation of OVA solution for initiating.

2 mg of OVA powder was weighed, dissolved with physiologic saline solution. The final volume was calibrated accurately to 14 mL.

3 Laboratory Animal and Breeding Environment 18 female SPF BALB/c mice (6 weeks old) were provided by Jinan pengyue laboratory animal breeding co. LTD. Animal production license number: SOCK (Lu) 2019-0003. Laboratory animal quality certificate No. 1107261911004850.

The mice were housed in a barrier system with 10,000 cleanliness level, at a temperature of 20-25° C., at a difference between day and night temperature ≤3° C., ventilation for 10-20 times per hour, at a relative humidity of 40-70%, with a pressure gradient of 20-50 Pa, in an artificial day/night cycle of 12 h: 12 h. Laboratory animal quality certificate No. SYXK (Lu) 20180031.

The feed was common granular diet irradiated with Cobalt-60 ($^{60}Co$), and originated from Beijing co. LTD.

4. Test Method

The mice were quarantined, adaptively fed, and divided into four groups: normal group, model group, positive control group and test group. Each group had 4 mice labeled as No. 1, No. 2, No. 3 and No. 4, respectively. The rest two mice were as backup.

The model group, positive control group and test group were administered with OVA solution through abdominal cavity to induce sensitization. Each mouse was administered with 0.2 mL of OVA solution containing 25 µg of OVA and 1 mg of aluminum hydroxide. Normal group as a control was injected with physiological saline solution at a dosage of 0.2 mL per mouse, where the first injection was labeled as D0, and the second injection and the third injection were performed on D7 and D14, respectively.

After induction, the drugs were administered to initiate sensitization. The test product was smeared on the noses of the mice in normal group 6 times each day. After application of the test product each day, 20 µL of physiological saline solution was dripped into the nasal cavity of the mice in normal group as a control, at a dosage of 10 µL per nostril. The physiological saline solution was smeared on the nose of the mice in model group 6 times each day. 5 µL of Levocabastine was dripped into the nasal cavity of the mice in positive control group 2 times each day, at a dosage of 2.5 µL per nostril. The test product was smeared on the noses of the mice in test group 6 times each day. After administration of the drugs each day, 20 µL of the OVA solution for sensitization was dripped into the nasal cavity of the mice in model group, positive control group and test group, respectively, at a dosage of 10 µL per nostril.

Daily administration was continued for 10 days from D20-D30. On D23, D27 and D30 (that is, the $3^{rd}$ day, $7^{th}$ day and $10^{th}$ day after administration), the number of times mice sneezed in each group within 15 min after administration was counted.

5. Statistical Analysis

Unpaired two-tailed t-test was used to analyze data for each group.

6. Test Result 6.1 Individual Mouse Data

TABLE 4

Individual mouse data for sneeze number.

|  | No. | Normal group | Model group | Positive control group | Test group |
|---|---|---|---|---|---|
| D23 | 1 | 4 | 22 | 15 | 18 |
|  | 2 | 5 | 22 | 8 | 12 |
|  | 3 | 9 | 25 | 11 | 8 |
|  | 4 | 7 | 22 | 7 | 8 |
| D27 | 1 | 8 | 58 | 75 | 52 |
|  | 2 | 5 | 79 | 45 | 37 |
|  | 3 | 12 | 89 | 44 | 44 |
|  | 4 | 10 | 53 | 22 | 26 |
| D30 | 1 | 9 | 118 | 124 | 89 |
|  | 2 | 7 | 91 | 108 | 92 |
|  | 3 | 13 | 105 | 46 | 82 |
|  | 4 | 10 | 87 | 110 | 42 |

6.2 Statistics and Graphs for Mice Detection

The statistical data of sneeze number of the mice is shown in Table 5.

Note: compared with the model group, *$P<0.05$, $P<0.01$, *$P<0.001$.

TABLE 5

Statistical data of sneeze number of mice

|  | Normal group | Model group | Positive control group | Test group |
|---|---|---|---|---|
| D23 | 6.25 ± 2.22*** | 22.75 ± 1.50 | 10.25 ± 3.59*** | 11.50 ± 4.73** |
| D27 | 8.75 ± 2.99*** | 69.75 ± 17.08 | 46.50 ± 21.76 | 39.75 ± 11.03* |
| D30 | 9.75 ± 2.50*** | 100.25 ± 14.13 | 97.00 ± 34.74 | 76.25 ± 23.21 |

Note:
compared with the model group,
*$P < 0.05$,
**$P < 0.01$,
***$P < 0.001$.

7. Discussion 7.1 The statistical results showed that the sneeze number of the mice in the model group increased significantly ($P<0.001$) compared with the normal group, illustrating that the model of allergic rhinitis in BALB/c mice was established successfully. In the test group, the sneeze number of the mice decreased significantly ($P<0.01$; $P<0.05$) on the 3$^{rd}$ day and the 7$^{th}$ day of administration compared with the model group, illustrating that the test product had a therapeutic effect on the allergic rhinitis of the mice. On the 10$^{th}$ day of administration, the test group showed a downward trend in the sneeze number compared with the model group, but no significant difference. The sneeze number of the mice in the positive control group decreased significantly ($P<0.001$) on the 3$^{rd}$ day of administration compared with model group, illustrating that levocabastine as a positive drug had a therapeutic effect on the allergic rhinitis in mice. On the 7$^{th}$ day and the 10$^{th}$ day of administration, the mice in positive control group had a downward trend in the sneeze number compared with model group, but no significant difference.

7.2 When the allergic rhinitis of the mice was initiated over time, the number of times of sneezing of the mice increased, the effect of the positive drug levocabastine and the test product were also decreased. The analysis of the individual mouse data showed that in the late stage of administration, the disease differentiated, and the reduction of sneezing frequency in some mice was low or not decreased, which may be related to the exacerbation of allergic rhinitis of the mice.

8. The test product has a desirable therapeutic effect on allergic rhinitis.

It will be obvious to those skilled in the art that changes and modifications may be made, and therefore, the aim in the appended claims is to cover all such changes and modifications.

What is claimed is:

1. A nasal balm for treating sneezing in a human in need thereof, consisting essentially of, by weight:
   10-50% of shea butter;
   10-50% of coconut oil;
   10-50% of Cera alba;
   1-5% of grapefruit peel oil;
   1-10% of Sclerocarya birrea seed oil;
   1-10% of Moringa pterygosperma seed oil; and
   1-10% of Simmondsia chinensis seed oil;
   wherein, the shea butter is cold pressed and unrefined solid;
   the coconut oil, the grapefruit peel oil, the Sclerocarya birrea seed oil, the Moringa pterygosperma seed oil, and the Simmondsia chinensis seed oil are extracted by cold compression method.

2. The nasal balm of claim 1, which consists essentially of the following ingredients by weight:
   20% of shea butter;
   40% of coconut oil;
   20% of Cera alba;
   1% of grapefruit peel oil;
   10% of Sclerocarya birrea seed oil;
   5% of Moringa pterygosperma seed oil; and
   4% of Simmondsia chinensis seed oil.

3. The nasal balm of claim 1, which consists essentially of the following ingredients by weight:
   10% of shea butter;
   50% of coconut oil;
   30% of Cera alba;
   4% of grapefruit peel oil;
   2% of Sclerocarya birrea seed oil;
   3% of Moringa pterygosperma seed oil; and
   1% of Simmondsia chinensis seed oil.

4. The nasal balm of claim 1, which consists essentially of the following ingredients by weight:
   50% of shea butter;
   10% of coconut oil;
   10% of Cera alba;
   4% of grapefruit peel oil;
   6% of Sclerocarya birrea seed oil;
   10% of Moringa pterygosperma seed oil; and
   10% of Simmondsia chinensis seed oil.

5. The nasal balm of claim 1, which consists essentially of the following ingredients by weight:
   15% of shea butter;
   25% of coconut oil;
   50% of Cera alba;
   3% of grapefruit peel oil;
   1% of Sclerocarya birrea seed oil;
   1% of Moringa pterygosperma seed oil; and
   5% of Simmondsia chinensis seed oil.

6. The nasal balm of claim 1, which consists essentially of the following ingredients by weight:
   20% of shea butter;
   40% of coconut oil;
   20% of Cera alba;

1% of grapefruit peel oil;
9% of *Sclerocarya birrea* seed oil;
5% of *Moringa pterygosperma* seed oil; and
4% of *Simmondsia chinensis* seed oil.

7. The nasal balm of claim 1, which consists of the following ingredients by weight:
10-50% of shea butter;
10-50% of coconut oil;
10-50% of *Cera alba;*
1-5% of grapefruit peel oil;
1-10% of *Sclerocarya birrea* seed oil;
1-10% of *Moringa pterygosperma* seed oil; and
1-10% of *Simmondsia chinensis* seed oil.

\* \* \* \* \*